United States Patent [19]

Ball

[11] Patent Number: 5,134,886
[45] Date of Patent: Aug. 4, 1992

[54] CAPACITIVE PRESSURE TRANSDUCER FOR USE IN RESPIRATOR APPARATUS

[76] Inventor: Kenneth H. Ball, 30003 Via Victoria, Rancho Palos Verdes, Calif. 90274

[21] Appl. No.: 685,687

[22] Filed: Apr. 16, 1991

[51] Int. Cl.$^5$ ............................................. G01L 9/12
[52] U.S. Cl. .............................. 73/718; 128/204.23; 128/716; 361/283
[58] Field of Search .................. 73/718, 724; 361/283; 128/204.23, 204.26, 716, 722

[56] References Cited

U.S. PATENT DOCUMENTS 5,052,400 10/1991 Dietz ................................. 128/722

Primary Examiner—Donald O. Woodiel
Attorney, Agent, or Firm—Edward A. Sokolski

[57] ABSTRACT

An electrically conductive diaphragm is sandwiched between a first and second board member. One of said board members has a metallic plate thereon, there being a non conductive spacer having an opening therein separating such board member from the diaphragm. The board members, diaphragm and spacer are joined together to form an integral assembly, the portion of the diaphragm opposite the opening in the spacer being free to move in such opening towards the board member with the metallic plate, motion of the diaphragm away from the spacer being prevented by the other board member. A respiratory gas inlet is provided through the board member with the metallic plate to the opening in the spacer. The diaphragm and metallic plate form a capacitor the capacitance of which is varied in response to the pressure differential between the gas inlet and the atmosphere, the diaphragm only being free to move towards the metallic plate in response to negative pressures (suction) induced during inspiration by a patient.

10 Claims, 3 Drawing Sheets

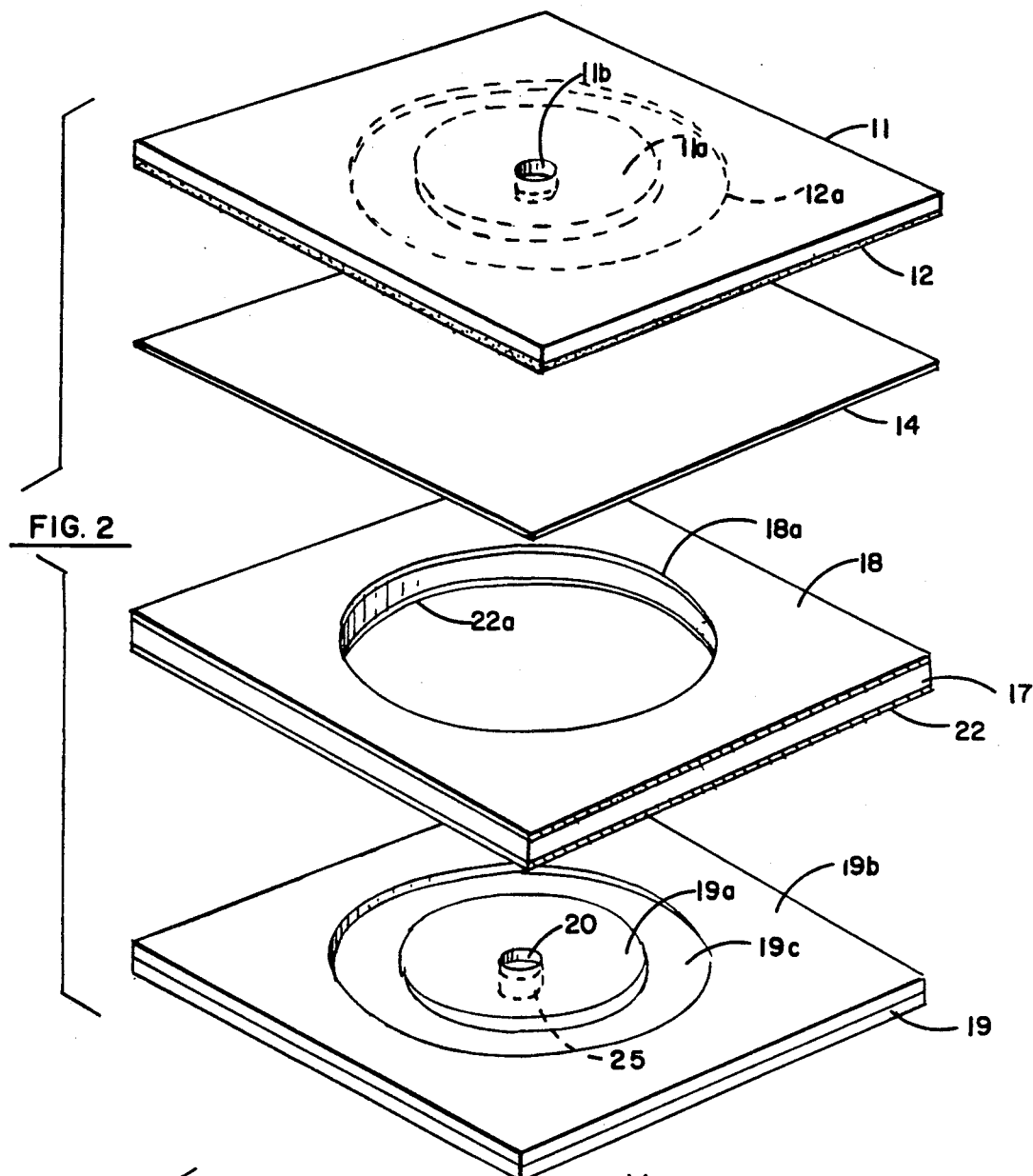
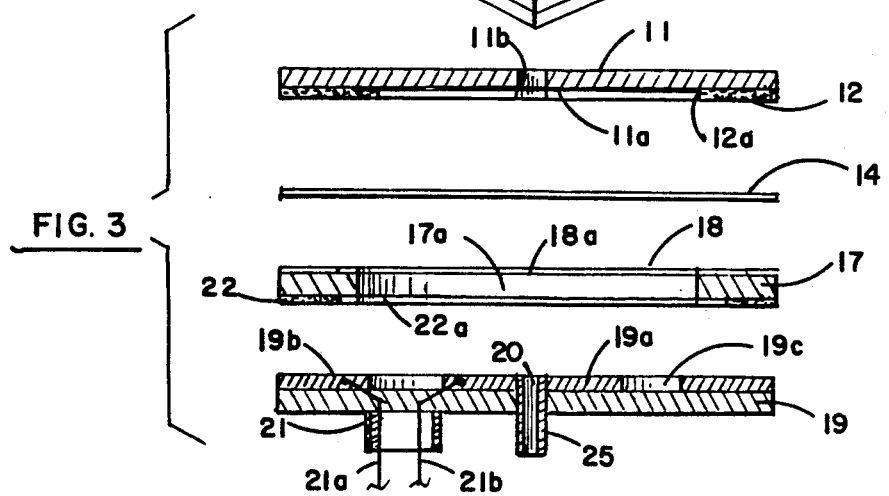
FIG. 2
FIG. 3

CAPACITIVE PRESSURE TRANSDUCER FOR USE IN RESPIRATOR APPARATUS

BACKGROUND OF THE INVENTION

1. Field of the Invention

This invention relates to capacitive pressure transducers and more to such a transducer for use in respirator apparatus which provides an electrical control signal for controlling the supply of a gas such as oxygen to a patient in response to the inspiratory breathing cycles of such patient.

2. Description of the Related Art

Respiratory Apparatus has been developed in the prior art which responds to the breathing cycles of the patient and supplies oxygen in response to such breathing cycles. In such devices, the breathing cycles are generally sensed by a pressure transducer which provides an electrical output in accordance with such breathing. Such an apparatus is described in U.S. Pat. No. 4,612,928 issued Sep. 23, 1986 to Tiep et al. Other such devices are described in the various references cited in the Tiep patent. The pressure transducers employed in such prior art devices generally operate in response to both the inspiration and expiration of the patient. As oxygen is to be supplied only in accordance with the inspiration demand of the patient, the expiration input is extraneous and it has been found tends to decrease the accuracy of the control signal for effecting the oxygen supply. This is particularly significant in the case of capacitive transducers in view of the fact that the diaphragm forming one of the capacitive plates of the transducer is driven in response to the expiration of the breathing cycle away from its neutral position and may return late to such position such that it will be seen by the system as an inspiration.

BRIEF SUMMARY OF THE INVENTION

The transducer of the present invention overcomes the aforementioned shortcomings of the prior art by employing a structure in which an electrical output is only provided in response to the inspiration cycles of the patient. Such structure comprises an electrically conductive diaphragm which is sandwiched between first and second board members. The first board member has a metal plate thereon which forms one of the plates of a capacitor, the other of the capacitor plates being formed by the diaphragm. A spacer board having an opening in the central portion thereof is placed between the diaphragm and the first board member such that the diaphragm is free to move axially in such opening towards and away from the first board member. The surface of the diaphragm opposite the second board member is mounted flush thereagainst with the entire diaphragm including the central portion thereof flat against the second board member. The various elements of the transducer are held together in a flat integrated unit by means of adhesive layers placed therebetween, the flexible diaphragm being held flat in its neutral position by such adhesive layers.

An inlet is provided through the first board member for receiving the respiratory pressure signal. The diaphragm is drawn towards the metal plate of the first board member in response to the inspiration cycles of the respiration. The diaphragm is, however, restrained against movement away from such plate by the second board member during the exhalation pressure inputs. A second metal plate is formed on the first board member which is electrically insulated from the first plate and which forms a fixed capacitor with the non-moving portions of the diaphragm, thus effectively providing an electrical connection to the diaphragm.

The capacitor formed by the transducer is connected in an electrical circuit in series with an oscillatory voltage such that the amplitude of such voltage is varied (modulated) in accordance with the inspiration breathing cycles, this in view of the change of capacitance and capacitive reactance in response to pressure changes induced by the inspiration cycles of the breathing of the patient.

It is therefore an object of this invention to provide a more accurate pressure transducer for use in a respirator system.

It is another object of this invention to provide a capacitive pressure transducer for use in a respirator system which responds only to the inspiration breathing cycles.

Other objects of the invention will become apparent from the following description in connection with the accompanying drawings.

BRIEF DESCRIPTION OF THE DRAWINGS

FIG. 2 is an exploded perspective view of a preferred embodiment of the invention;

FIG. 3 is an exploded elevational view in cross section of the preferred embodiment;

DETAILED DESCRIPTION OF THE INVENTION

Figure 1A:
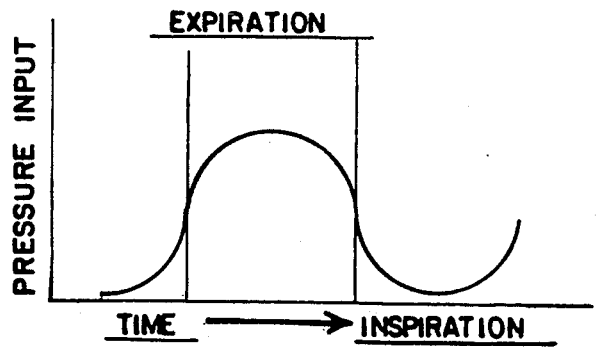
FIG. 1 is a graphic illustration of the respiratory pressure input generated by breathing.
FIG. 1B is a graphic illustration of the operation of prior art transducers.
FIG. 1C is a graphic illustration of the operation of the transducer of the present invention.
Figure 1B:
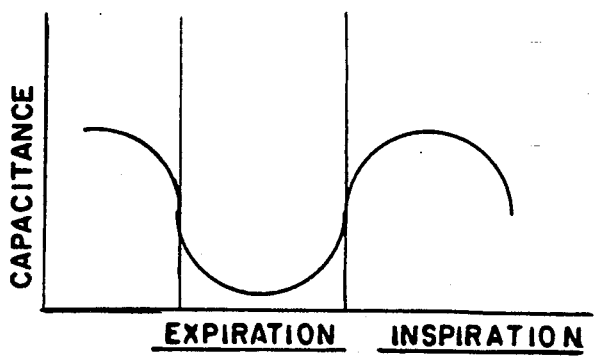
Figure 1C:
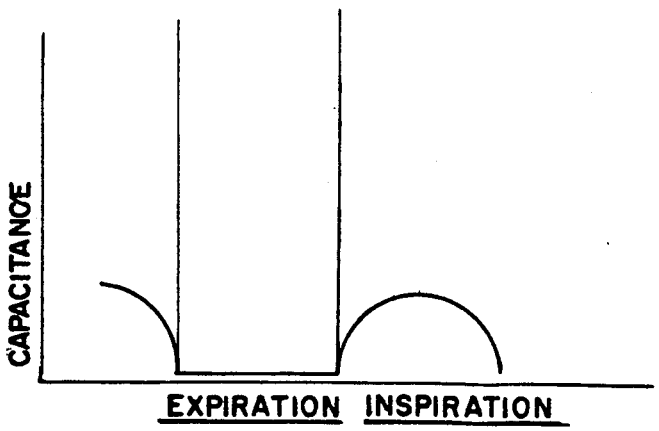

Referring now to FIGS. 1A-1C, waveforms illustrating the operation of the invention are shown. FIG. 1A shows the pressure input to a pressure transducer in response to the breathing of a patient. As can be seen, the variation in pressure is approximately sinusoidal with the inspiration portions of the breathing cycle producing a negative pressure (suction) and the expiration portions of the breathing cycle producing a positive pressure.

Referring now to FIG. 1B, the variations in capacitance produced in response to the breathing cycles shown in FIG. 1A in a prior art pressure transducer are shown. As can be seen, the capacitance of the transducer output increases in response to inspiration and decreases in response to expiration. It is to be noted that this prior art transducer employs an electrically conductive diaphragm responsive to the breathing cycles which is drawn closer to a fixed conductive plate during inspiration and driven away from this fixed plate during expiration, the diaphragm and plate forming the plates of a capacitor.

Referring now to FIG. 1C, the operation of the invention is illustrated. As can be seen, the device of the invention responds only to the inspiration cycles and not to the expiration cycles. Thus, there is a transducer output reflecting an increase in capacitance and lowering of capacitive reactance only in response to the patient's inspiration. This, as pointed out above, enables the provision of a much more desirable supply of oxygen (or other gas) to the patient.

Figure 3A:
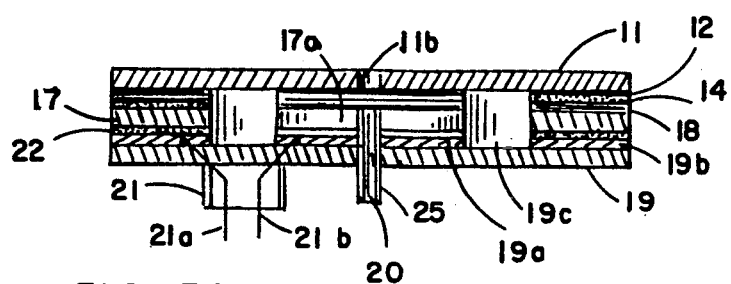
FIG. 3A is a cross sectional view of the preferred embodiment.

Referring now to FIGS. 2, 3 and 3A, a preferred embodiment of the invention is shown. Top board 11 which is of an electrically insulative material has a metal disc 11a formed on the center of the undersurface thereof, this end result typically being achieved by employing a copper clad printed circuit board for board 11 and etching away all but the disk portion. A vent hole 11b is formed through board 11 and disk 11a to maintain the top of diaphragm at atmospheric pressure. Adhesive layer 12 is placed between the undersurface of board 11 and diaphragm 14. Layer 12, which may be formed from no.9491 adhesive available from Minnesota Mining and Manufacturing Co., has a central circular aperture 12a formed therein which has the same diameter as apertures 18a and 22a. Adhesive layer 12 has the same thickness as disk 11a(typically of the order of 0.002 inches). Adhesive layer 12 thus acts as both a spacer and a binder for joining the diaphragm 14 to board 11.

Spacer member 17 has an aperture 17a formed in the center thereof which is approximately the same diameter as that of disk 11a (typically 1.1 inches). Spacer member 17 which is made of an electrically insulative material such as a polycarbonate plastic typically has a thickness of about 0.01 inches. Spacer member 17 is bound to the underside of diaphragm 14 by means of adhesive layer 18 which may be of the same material and thickness as adhesive layer 12. Adhesive layer 18 has a circular aperture 18a formed in the central portion thereof which mates with the aperture 17a of spacer 17. Diaphragm 14 is carefully installed between the opposing adhesive layers to assure that it lies flat therebetween. The diaphragm is of a non conductive plastic material such as polycarbonate with a thickness which is typically about 0.0005 inches. The top surface of the diaphragm which faces top board 11 is metalized with a material such a nickel to provide one of the plates of the capacitor of the transducer.

Bottom board 19 is a printed circuit board similar to top board 11. The copper cladding of this board is etched to form central disk 19a and outer plate 19b with a circular space 19c therebetween. An aperture 20 which runs through board 19 and disk 19a is provided and a pressure inlet tube 25 for receiving the breathing pressure of a patient is installed in this aperture. An electrical connector 21 is attached to board 19, this connector having a pair of electrical leads 21a and 21b which are connected to disk 19a and outer plate 19b, respectively. Board 19 is bound to spacer 17 by means of adhesive layer 22 which is similar to adhesive layers 12 and 18 and has a circular aperture 22a formed in the central portion thereof.

It is to be noted that while in the preferred embodiment the device of the invention utilized flat boards, which are joined together by means of adhesive layers, the device can also be fabricated using sheets of electrically insulative material which are joined together by screws, rivets or other fastening means.

Figure 4:
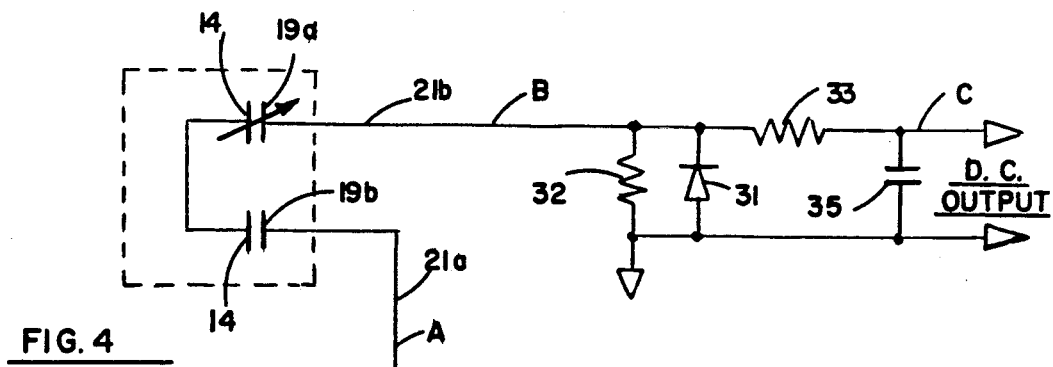
FIG. 4 is an electrical schematic drawing illustrating the operation of the transducer of the invention.

Referring now to FIGS. 4 and 5, an electrical circuit for generating a control signal from the output of the transducer of the invention is shown along with waveforms generated in such circuit.

The output of carrier wave generator 30 which may be a square wave generator and typically has a frequency of 200-600 kiloHz is fed to plate 19b of the transducer. A fixed capacitance appears between plate 19b and the opposing portions of diaphragm 14. This capacitance couples the output of the square wave generator to the diaphragm. A variable capacitor is formed between the disk 19a and the opposing central portions of the diaphragm. The central portions of the diaphragm are free to move towards disk 19a in the cavity 17a formed in spacer 17. The diaphragm is prevented from moving from its center position towards plate 11 by metal disk 11a and the opposing portions of adhesive layer 12. Thus, the diaphragm can only move in response to suction pressure as induced during inspiration and is prevented from moving away from its neutral position in response to expiration induced pressure.

Figure 5D:
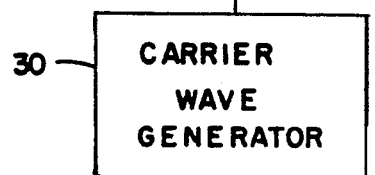
FIG. 5A-5E are a series of waveforms related to the drawing of FIG. 4.
Figure 5D:
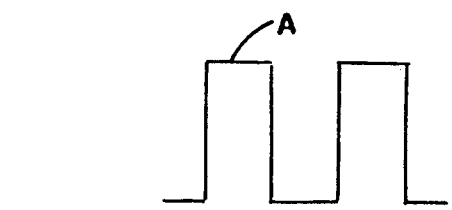
Figure 5A:
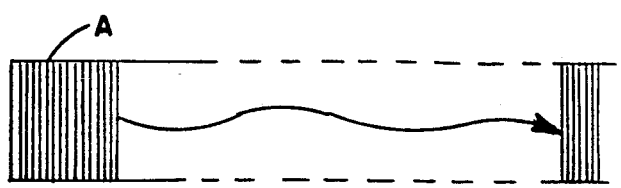
Figure 5E:
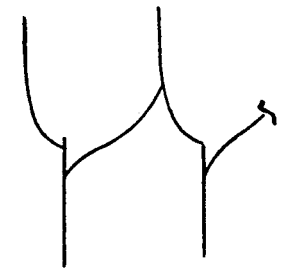
Figure 5B:
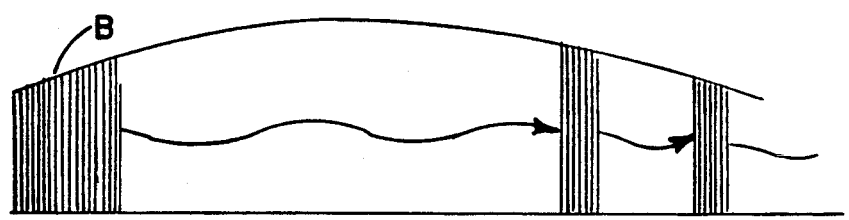
Figure 5C:
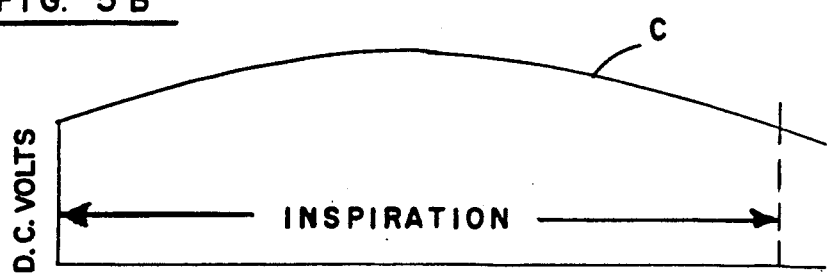

FIG. 5A schematically illustrates the square wave signal generated by generator 30 without there being any pressure input to the transducer to vary the capacitance of the capacitor formed between the diaphragm and disk 19a. FIG. 5B schematically illustrates a modulation or variation in amplitude of the square wave signal due to variations in the capacitance of the variable capacitor in response to a breathing inspiration induced input pressure. The individual square waves, as shown in FIG. 5D are differentiated to form sharp pulses as shown in FIG. 5E. This differentiation is effected by the differentiator formed by the fixed and variable capacitors and resistor 32. This differentiated signal has its negative going portions clipped by diode 31, and this signal is integrated in the integration circuit formed by resistor 33 and capacitor 35 to provide a varying DC output "C" as shown in FIG. 5C.

In this manner, a DC output signal is generated which is in accordance with the inspiration portions of the breathing cycle only and which has no output in response to expiration.

While the invention has been described and illustrated in detail, it is to be clearly understood that this is intended by way of illustration and example only and is not to be taken by way of limitation, the scope of the invention being limited only by the terms of the following claims.

I claim:

1. A capacitive pressure transducer for use in respirator apparatus comprising:
   first and second board members,
   a diaphragm having a conductive surface forming one of the plates of a capacitor, said diaphragm being mounted between said board members,
   said first board member having a conductive surface portion positioned opposite said diaphragm and forming the other of the plates of said capacitor, said diaphragm having a predetermined neutral position,
   means for restraining said diaphragm against movement from said neutral position away from said first board member,
   means for permitting movement of said diaphragm from said neutral position towards said first board member,
   means for joining said board members and said diaphragm together to form an integral assembly, and
   inlet means for introducing a respirator pressure signal through said first board member to said diaphragm, the diaphragm being restrained from movement away from said first board member during the expiration cycles of said pressure signal and being permitted to move towards said first board member during inspiration cycles of said pressure signal, thereby providing a variation in capacitance between the diaphragm and the conductive surface of said first board member solely in accordance with said inspiration cycles.

2. The capacitive pressure transducer of claim 1 wherein said means for permitting movement of said diaphragm towards said first board member comprises a spacer board having an opening therein mounted between the first board member and the diaphragm.

3. The capacitive pressure transducer of claim 1 wherein said means for restraining said diaphragm against movement away from said first board member comprises a surface of said second board member which is mounted flush against said diaphragm.

4. The capacitive pressure transducer of claim 2 wherein said means for restraining said diaphragm against movement away from said first board member comprises a surface of said second board member which is mounted flush against said diaphragm.

5. The capacitive pressure transducer of claim 2 wherein the means for joining the board members the diaphragm, and the spacer board together comprises a first adhesive layer between said first board member and said spacer board, a second adhesive layer between said spacer board and said diaphragm, and a third adhesive layer between said diaphragm and said second board member.

6. The capacitive transducer of claim 1 wherein said inlet means comprises a tube member extending through said first board member to provide fluid communications to said diaphragm.

7. A capacitive pressure transducer for use in respirator apparatus comprising:
    first and second members, each of said members having at least one substantially flat surface,
    a diaphragm having a conductive surface forming one of the plates of a capacitor, said diaphragm being mounted between the one flat surface of said members and having a predetermined neutral position,
    said first member having a conductive surface on said one flat surface thereof, said conductive surface being positioned opposite said diaphragm and forming the other of the plates of said capacitor,
    spacer means having an opening therein mounted between the first member and the diaphragm,
    said one flat surface of the second member being mounted flush against said diaphragm so as to prevent motion of said diaphragm from said neutral position towards said second board member,
    means for joining said members, said diaphragm and said spacer means together to form an integral assembly, and
    inlet means for introducing a respiratory pressure signal through the first member to the opening in said spacer means, the diaphragm being in said neutral position restrained against movement away from said first member during expiration cycles of said respirator pressure signal and being permitted to move towards said first member during inspiration cycles of said respirator pressure signal, thereby providing a variation in capacitance between the diaphragm and the conductive surface of said first member solely in accordance with said inspiration cycles.

8. The capacitive pressure transducer of claim 7 wherein the means for joining the members, the diaphragm and the spacer means together comprises a first adhesive layer between said first member and said spacer means, a second adhesive layer between said spacer means and said diaphragm, and a third adhesive layer between said diaphragm and said second member.

9. The capacitive pressure transducer of claim 7 wherein said inlet means comprises a tube member extending through said first board member to provide fluid communications to said diaphragm.

10. A capacitive pressure transducer for use in respirator apparatus comprising:
    first and second members, each of said members having at least one substantially flat surface,
    a diaphragm having a conductive surface forming one of the plates of a capacitor, said diaphragm being mounted between the one flat surface of said members and having a predetermined neutral position,
    said first member having a conductive surface on said one flat surface thereof, said conductive surface being positioned opposite said diaphragm and forming the other of the plates of said capacitor,.
    spacer means having an opening therein mounted between the first member and the diaphragm,
    said one flat surface of the second member being mounted flush against said diaphragm so as to prevent motion of said diaphragm from said neutral position towards said second board member,
    said first member having a second conductive surface on said one flat surface thereof which is independent of said first mentioned conductive surface, said second conductive surface forming a fixed capacitor with the portions of said diaphragm which are not opposite the opening in said spacer means,
    means for joining said members, said diaphragm and said spacer means together to form an integral assembly, and
    inlet means for introducing a respiratory pressure signal through the first member to the opening in said spacer means, the diaphragm being in said neutral position restrained against movement away from said first member during expiration cycles of said respirator pressure signal and being permitted to move towards said first member during inspiration cycles of said respiratory pressure signal, thereby providing a variation in capacitance between the diaphragm and the conductive surface of said first member solely in accordance with said inspiration cycles.

* * * * *